US012270783B2

United States Patent
Schicht et al.

(10) Patent No.: US 12,270,783 B2
(45) Date of Patent: Apr. 8, 2025

(54) SINGLE CELL GEL ELECTROPHORESIS

(71) Applicant: 4D Lifetec AG, Cham (CH)

(72) Inventors: Oliver Schicht, Baar (CH); Arne-Christian Faisst, Oberdorf (CH)

(73) Assignee: 4D LIFETEC AG, Cham (CH)

( * ) Notice: Subject to any disclaimer, the term of this patent is extended or adjusted under 35 U.S.C. 154(b) by 983 days.

(21) Appl. No.: 16/960,124

(22) PCT Filed: Jan. 8, 2019

(86) PCT No.: PCT/EP2019/050335
§ 371 (c)(1),
(2) Date: Jul. 6, 2020

(87) PCT Pub. No.: WO2019/135008
PCT Pub. Date: Jul. 11, 2019

(65) Prior Publication Data
US 2021/0063348 A1  Mar. 4, 2021

(30) Foreign Application Priority Data
Jan. 8, 2018 (EP) ..................... 18150558

(51) Int. Cl.
*G01N 27/447* (2006.01)
*C12N 15/10* (2006.01)
(Continued)

(52) U.S. Cl.
CPC ......... *G01N 27/44756* (2013.01); *C12Q 1/68* (2013.01); *G01N 33/48721* (2013.01)

(58) Field of Classification Search
CPC ........... G01N 27/44756; G01N 27/453; G01N 33/48721; C12Q 1/68; C12N 15/101
See application file for complete search history.

(56) References Cited

U.S. PATENT DOCUMENTS

2003/0175821 A1  9/2003  Hoover et al.
2012/0058467 A1  3/2012  Thomas et al.

FOREIGN PATENT DOCUMENTS

WO    WO 2005087208 A2 *  9/2005  ............ A61K 31/01
WO    2016/141495           9/2016

OTHER PUBLICATIONS

Duthie et al., "Antioxidant Supplementation Decreases Oxidative DNA Damage in Human Lymphocytes," Cancer Research 56. 1291-1295, Mar. 15, 1996 (Year: 1996).*

(Continued)

*Primary Examiner* — Alexander S Noguerola
(74) *Attorney, Agent, or Firm* — Rankin, Hill & Clark LLP

(57) ABSTRACT

A carrier plate and a liquid sample are provided for the use of a single cell gel electrophoresis device for screening a subject for at least a DNA-damage, in particular a specific DNA-damage, in relation to a predisposition for and/or the presence of a disease. The liquid sample has cells of the subject. A single cell gel electrophoresis on the sample of the subject is performed by positioning the sample accommodated on the carrier plate in the generated homogenous electrical field and controlling strength and direction of the electrical field while the sample is positioned in the gel electrophoresis device. The DNA-damage is determined with a high reproducibility, with a coefficient of variation (CV) of 15% or less, in particular 10% or less, in particular 5% or less.

16 Claims, 3 Drawing Sheets

(51) Int. Cl.
*C12Q 1/68* (2018.01)
*G01N 33/487* (2006.01)

(56) References Cited

OTHER PUBLICATIONS

Karbaschi et al., "Novel method for high-throughput processing of slides for the comet assay," Scientific reports|4:7200|DOI:10.1038/srep07200, pp. 1-6 (Year: 2014).*

Speit et al., "The Comet Assay: A Sensitive Genotoxicity Test for the Detection of DNA Damage and Repair," from Methods in Molecular Biology: DNA Repair Protocols: Mammalian Systems, Second Edition Edited by: D. S. Henderson © Humana Press Inc., Totowa, NJ, published 2006 (Year: 2006).*

Hervé Abdi, "Coefficient of Variation," in Neil Salkind (Ed.), Encyclopedia of Research Design, Thousand Oaks, CA: Sage. 2010 (Year: 2010).*

Lovell et al., "Issues Related to the Experimental Design and Subsequent Statistical Analysis of In Vivo and In Vitro Comet Studies," Teratogenesis, Carcinogenesis, and Mutagenesis 19:109-119 (1999) (Year: 1999).*

Wiklund et al., "Aspects of design and statistical analysis in the Comet Assay," Mutagenesis vol. 18 no. 2 pp. 167-175, 2003 (Year: 2003).*

Ge et al., "Micropatterned comet assay enables high throughput and sensitive DNA damage quantification," Mutagenesis, 2015, 30, 11-19 (Year: 2015).*

Collins et a;, "Oxidation of Celular DNA Measured with the Comet Assay," from Methods Mol. Biol. 2002; vol. 186:147-59 (Year: 2002).*

EPO machine-generated English language translation of WO 2016/141495 A2, patent published Sep. 15, 2016, translation downloaded Aug. 5, 2023 (Year: 2016).*

Signe Braafladt et al., "The Comet Assay: Automated Imaging Methods for Improved Analysis and Reproducibility", Scientific Reports, Sep. 1, 2016, vol. 6, No. 1, pp. 1-9; Cited in International Search Report; discussed in specification.

Ulla Plappert-Helbig et al., "Inter-Laboratory Comparison of the In Vivo Comet Assay Including Three Image Analysis Systems", Environmental and Molecular Mutagenesis (2015), pp. 788-793; Discussed in specification.

Amaya Azqueta et al., "A comparative performance test of standard, medium- and high-throughput comet assays", Toxicology in Vitro (2013), vol. 27, pp. 768-773; Discussed in specification.

Andrew R. Collins et al., "Controlling variation in the comet assay", frontiers in GENETICS, Oct. 20, 2014, vol. 5 Article 359, pp. 1-6; Discussed in specification.

Benjamin M. Gyori et al., "OpenComet: An automated tool for comet assay image analysis", Redox Biology, (2014), vol. 2, pp. 457-465; Discussed in specification.

* cited by examiner

SINGLE CELL GEL ELECTROPHORESIS

BACKGROUND OF THE INVENTION

Field of the Invention

The invention relates to the field of chemical and molecular-biological analysis, in particular to the field of screening. It relates to a use of a single cell gel electrophoresis device for and/or a method of screening a subject.

Description of Related Art

Single cell gel electrophoresis, also called comet assay, is a sensitive method for the direct detection of DNA single-strand breaks and double-strand breaks that can arise due to different causes, such as, for example, due to the influence of environmental toxins, due to chemical reactions as a result of taking medicine or generally due to chemical reagents that react with DNA. Physical influences such as ionising radiation either alone or in interaction with chemical reagents can cause damage to DNA.

Individual cells can be subjected to a gel electrophoresis with the help of single cell gel electrophoresis, also called "comet assay" for detecting DNA damage. The cells that are to be examined or treated can be embedded, e.g., into agarose, and can be deposited as so-called gel spots onto a carrier material such as, for example, onto an object carrier or film, lysed and either treated in an alkaline manner in order to denature the DNA or however kept in a neutral environment. The subsequent electrophoresis leads to the fragmented DNA removing itself from the cell nucleus due to the formation of an electrical field, i.e. the negatively charged DNA fragments travel to the plus pole and here produce a co-called "comet". The quantity of DNA that has drifted out of the head of the comet into the tail is quantified and serves as a measure of the DNA damage present in the sample. The quantification is mostly effected by way of fluorescence microscopy and is implemented in a manual, partly automated or fully automated manner. Gel electrophoresis systems are known, e.g. from WO 2016/141 495.

Although the conventional gel electrophoresis systems for comet assays provide acceptable results, however, over and over it has been found that the results can vary greatly from laboratory to laboratory, from user to user in the same laboratory and even from gel to gel and assay to assay, and for example the same sample in an independent examination in 12 different laboratories can result in a DNA damage of 20% up to 80%, which corresponds to a factor of four. The reason for such a low reproducibility can be found in the preparation of the gel spots (samples) as well as the non-standardised electrophoresis conditions for the gels, such as, for example, fluctuations in the temperature of the buffer solution during the electrophoresis, in the distance between the electrodes and/or in the buffer height and in the content of ions of the buffer above the gel spots.

ULLA PLAPPERT-HELBIG ET AL; "Inter-laboratory comparison of the in vivo comet assay including three image analysis systems: Comparison of the In vivo Comet Assay", ENVIRONMENTAL AND MOLECULAR MUTAGENESIS, vol. 56, no. 9, 6 Aug. 2015 (2015-08-06), pages 788-793 discloses a comparison for different comet assays. Nevertheless, the reproduction of the test results are rather poor, when analysing the comet assays is done in an automated manner. With human optimization interaction the error and/or variation of the scoring of the samples can be minimised as human interaction is always optimizing towards desired outcomes.

Alternative methods for detecting DNA damage are known from US 2012/058467. Plates including electrodes directly in wells are used to provide a high-throughput, automated comet assay for detecting DNA damage.

The intensity of the comet tail relative to the head reflects the number of DNA breaks. In order to visualise the comet the spots staining of DNA is performed and the fluorescence is calculated to determine the extent of DNA damage.

SUMMARY OF THE INVENTION

It is therefore an object of the invention to create a possibility of screening a subject for at least a DNA-damage in relation to a predisposition for and/or a presence of a disease which overcomes the disadvantages mentioned.

These objects are achieved by a the use of a single cell gel electrophoresis device for screening a subject for at least a DNA-damage in relation to a predisposition for and/or a presence of a disease and a method to method for screening a subject for at least a DNA-damage in relation to a predisposition for and/or a presence of a disease.

For the use of a single cell gel electrophoresis device for screening a subject for at least a DNA-damage, in particular a specific DNA-damage, in relation to a predisposition for and/or the presence of a disease a carrier plate and a liquid sample is provided. The liquid sample includes cells of the subject.

A single cell gel electrophoresis on the sample of the subject is performed by:
positioning the sample accommodated on the carrier plate in the generated homogenous electrical field and
controlling strength and direction of the electrical field while the sample is positioned in the gel electrophoresis device.

The DNA-damage is determined with a high reproducibility, with a coefficient of variation (CV) of 15% or less, in particular 10% or less, in particular 5% or less.

The coefficient of variation (CV) is a measure for the standard deviation of a set of data with a changing means value. The coefficient of variation can be defined as the ratio of the standard deviation and the mean value. Accordingly, it can be viewed as the extent of variability in relation to the mean of the population. In cases when the mean value is close to zero, the coefficient of variation will approach infinity and is therefore sensitive to small changes in the mean.

A technical respectively physical variation/variance is observed for the same sample respectively the same aliquot. In contrast to that biological variation/variance originates from the properties of the sample respectively from the predisposition for and/or the presence of a disease.

Prior art documents as Azqueta et al.: A comparative performance test of standard, medium- and high-throughput comet assays; Toxicology in Vitro, volume 27, pp. 768-773, 2013 (short: Azqueta et al.) and Collins et al.: Controlling variation in the comet assay; frontiers in Genetics, volume 5, article 359, October 2014 (short: Collins et al.) describe the current common knowledge of standardisation and potential for optimisation regarding the precision of the comet assay/single cell gel electrophoresis (SCGE).

Collins et al. describes a method for standardising the treatment of the tested cells. Two partner laboratories (short: labs) carried out experiments with TK-6 lymphoblastoid cells treated with 0.25 mM methylmethanesulphonate (MMS) for 3 h. Furthermore the sample is biological influenced and therefore not applicable to an arbitrary experiment, but is manipulating the biological properties of the cells. This limits the application of Collins method for usage in real screening a subject for a DNA-damage in relation to a predisposition and/or presence of a disease. Such a manipulation depends to a high degree on the activity and specificity of the enzyme used for the treatment of the cells, as for example formamidopyrimidine DNA glycosylase (FPG) converts 8-oxoguanine and some other oxidised purines to breaks. Depending on the enzyme more or less breaks are produced, which are building the comet in the evaluated comet assays.

As stated by Collins et al. page 3, right column: "one laboratory had more variable results than the other". According to data shown by Collins the determined DNA-damage between two labs differs roughly by a factor of 2 to 3 meaning by roughly 30%. Such a coefficient of variation CV can be also called lab-to-lab coefficient of variation. The lab-to-lab CV can be view as inter-laboratory comparison giving an inside on the actual reproducibility of the determined DNA-damage.

In contrast to that the a lab-to-lab coefficient of variation (CV) can be 15% or less, in particular 10% or less, in particular 8% or less, in particular 7.5% or less, in particular 5% or less, in particular 3% or less, in particular 2% or less, in particular 1% or less. This enables a comparability of the determined DNA-damage not only within one laboratory.

Due to the high reproducibility a biological variance in the screened liquid sample of the subject can be evaluated. In contrast to that, according to the prior art the biological variance is covered by the variation of the single cell gel electrophoresis and the subsequent determination of the DNA-damage. The high reproducibility makes the use of the screening according to the invention reliable and applicable to other systems and evaluations. The low lab-to-lab coefficient of variation enables a determination of the DNA-damage and a corresponding screening of a subject for a DNA-damage in relation to a predisposition for and/or a presence of a disease.

Based on the high variation between the different labs, Collins' data require an internal standard, as already mentioned by Collins. This is not the case for the highly standardised and highly reproducible method and use according to the invention, which offers a timely stable and homogenous field. The method can also include a well-defined and strict protocol including ready to use reagents. Any internal standard can only be used to make sure that the assay is working appropriate.

According to Collins et al. the data of the comet assay vary from spot-to-spot quiet significantly (FIG. 3 of Collins et al.). In contrast to that the reproducibility on a spot-to-spot basis can be improved according to the present invention. The spot-to-spot coefficient of variation (CV) can be 15% or less, in particular 10% or less, in particular 8% or less, in particular 7.5% or less, in particular 5% or less, in particular 3% or less, in particular 2% or less, in particular 1% or less. In this context spot-to-spot CV can be viewed as variation of the determined DNA-damage on a spot-to-spot basis. A spot being one liquid sample respectively one aliquot of the liquid sample screened.

Furthermore, also an evaluation of the DNA-damage on a plate-to-plate basis can give rise to a coefficient of variation (CV) that can be 15% or less, in particular 10% or less, in particular 8% or less, in particular 7.5% or less, in particular 5% or less, in particular 3% or less, in particular 2% or less, in particular 1% or less. The plate-to-plate CV can be determined form single spots (aliquots) arranged on different carrier plates.

State of the art determination of a DNA-damage can be performed on none manipulated cell sample with an average damage with a coefficient of variation of approximately 30-40%. According to the claimed invention the coefficient of variation (CV) of 15% or less can also be obtained. Such a CV can also be obtained in disproportionally (over- or underproportionally) damaged cells, as for example a simulated damage introduced by X-ray.

It is possible that the lab-to-lab, the plate-to-plate and the spot-to-spot coefficient of variation can be 15% or less, in particular 10% or less, in particular 8% or less, in particular 7.5% or less, in particular 5% or less, in particular 3% or less, in particular 2% or less, in particular 1% or less. As mentioned above, it is also possible that the lab-to-lab, the plate-to-plate and the spot-to-spot coefficient of variation independently from each other can be 15% or less, in particular 10% or less, in particular 8% or less, in particular 7.5% or less, in particular 5% or less, in particular 3% or less, in particular 2% or less, in particular 1% or less. In other words: the lab-to-lab, the plate-to-plate and/or the spot-to-spot coefficient of variation can be 15% or less, in particular 10% or less, in particular 8% or less, in particular 7.5% or less, in particular 5% or less, in particular 3% or less, in particular 2% or less, in particular 1% or less.

The liquid sample can include cells and/or cell types of cell of cell lines and/or patient namely the subject. The liquid sample can be a blood sample. The liquid sample can include a sample/cells of a biopsy (for example, tissue), cancer cells, tumour cells. The sample respectively the obtained cells can be transferred into the liquid sample. In other words: The origin of the sample respectively the cells to be screened is not decisive for the liquid sample.

The gel electrophoresis device can be capable of at least one of:
positioning at least one carrier plate in a homogenous electrical field generated by at least one pair of electrodes; and
controlling strength and direction of the electrical field generated at the position of the samples accommodated on the carrier plate.

This enables a controlled environment during the performance of the single cell gel electrophoresis (SCGE).

The single cell gel electrophoresis device can also be capable to ensure an unidirectional positioning of the carrier plate respectively the sample in the device leading to a defined effective direction of the electrical field acting on the sample. The single cell gel electrophoresis device can be equipped for mounting one or more samples on one or more substrates in the single cell gel electrophoresis device. The gel electrophoresis device can be configured such that the at least one carrier plate can be immersed into a gel electrophoresis buffer which is located in the device. The gel electrophoresis buffer can flow freely around the carrier plate, for example after the closure of a lid. The single cell gel electrophoresis (SCGE) can be performed by utilising the properties of the single cell gel electrophoresis device.

The carrier plate can include a hydrophilic surface. The hydrophilic surface enables a fixation of the sample on the carrier plate. The carrier plate does not have to be a solid plate. It can also be a foil element capable to carry the sample.

In other embodiments the single cell gel electrophoresis device can be used for screening of genetic toxins.

Due to the measurement of the DNA breakages it can be possible to determine the substance, respectively, toxin, which was in contact with the cells.

Several toxicities are possible. For example, a substance can be toxic to a cell without attacking the DNA.

The gel electrophoresis device can include further components.

The gel electrophoresis system can include
an integrated means for the temperature control and/or
an integrated means for cooling and/or heat production, in particular for maintaining a constant temperature in the gel electrophoresis device during the gel electrophoresis procedure.

The gel electrophoresis device can include an integrated means for the buffer circulation, in particular an integrated means for the buffer circulation, by way of which means a uniform ion distribution and temperature distribution in the buffer solution can be ensured during electrophoresis.

The gel electrophoresis system can also include
an integrated voltage generating device and/or
an integrated mains connection device and/or
an integrative software and/or
a subsequently arranged, integrated and automated analysis device for the quantification of the obtained results and/or
a digital interface for the further processing of the results.

Data of measuring electrodes and/or data of a means for the temperature control can be acquired and optionally recorded by a software that can be integrated in the gel electrophoresis device. The software can control and/or regulate a means for the voltage generation, a means for the buffer circulation and/or a means for cooling and heat production, on the basis of this data. Should the measured values deviate from a given value range, the software can control the means specified above such that values which deviate from the set points are corrected. In this manner, it is possible to keep parameters within a certain parameter range, in particular essentially constant, during the complete electrophoresis procedure. Constant conditions, for example a constant electrical field in the region of the carrier plates with the gel spots can be ensured by way of this.

The subject can be screened for a specific DNA-damage. This can enable the screening for a specific disease.

The screening can be performed on at least two aliquots of the subject liquid sample. Per aliquot at least 75-100 cells can be evaluated. This can build a basis for evaluating the reproducibility of the single cell gel electrophoresis and the corresponding screening.

According to the present invention it can be also possible to count respectively evaluate 200 to 400 cells per aliquot. Per aliquot 75 to 400 cells can be evaluated to determine the DNA-damage, in particular at least one of 100 to 400, 200 to 400, 75 to 200, 100 to 200, and 75 to 100 cells per aliquot can be evaluated to determine the DNA-damage. This enables the reduction of aliquots required for reliably evaluate the reproducibility and the result of the single cell gel electrophoresis and/or the screening. According to the prior art bigger amounts of cells, e.g. at least 1000 cells per sample, are evaluated as known e.g. from US 2003/175821. A reduced number of cells to be evaluated can reduce the time needed to reliably determine the DNA damage leading to the possibility to obtain a high throughput.

An aliquot can be a fraction of the sample to be screened. The subdivision of the sample can allow for multiple and/or repeated evaluation of the sample.

One aliquot can be a control sample respectively a standard sample for verification of the testing/screening conditions.

A biological variance between different screened subjects can be determined. The biological variance can be determined between the subject's results and the results of a screened population. Such a screening of a population can be called biomonitoring.

In other words: the biological variability can be observed across samples of the subjects, such as individuals, within a population.

The determination of the biological variance can lead to a better understanding of the processes involved for DNA-damage and enables the mathematical description and modelling of the observed phenomena.

The biological variance is superimposed with the physical variance. According to the present invention the physical variance can be minimised compared to the state of the art in order to determine the biological variance of the sample. This becomes evident when comparing results obtained from different labs respectively institutes for the same sample respectively a standard sample.

The biological variance can be influence by several factors, for example stress induced to the subject, e.g., a 5000 m endurance run. The biological properties of the cells can influence the effectiveness of a therapy.

The sample of the subject or components thereof can be treated with at least one enzyme related to a biomarker. Such a biomarker can be a biomarker for cancer—enabling a biomarker assay for the evidence of cancer.

The biological variance and/or determined DNA-damage is capable to indicates a predisposition for and/or the presence of the disease, in particular for a specific type of disease, a cancer, aggressiveness of cancer, environmental variation of biological response of a cell line, effectiveness of a therapy.

Before performing the single cell gel electrophoresis the cells of the liquid sample can be separated in individual fractions and/or types of cells. This enables the determination the DNA-damage in a specific type of separated cells. The single cell gel electrophoresis can be performed on lymphocytes and/or biomarker carrier cells. This can allow for a specific diagnostic/determination of the DNA-damage.

The sample of the subject can be obtained from a whole blood sample of the subject, as described above. A plurality of samples can be taken as a jointed single sample from the subject. The whole blood sample can include peripheral whole blood.

One or more samples can be mounted on one or more substrates respectively carrier plates.

The liquid sample accommodated on the carrier plate can be not flattened and/or not levelled on the carrier plate. In other words: The liquid sample accommodated on the carrier plate is not squeezed, e.g., by a cover plate and/or cover slide. Accordingly, the liquid sample is not artificially spread over carrier plate, resulting in a focused spot on the carrier plate.

The determination of the DNA-damage can be performed in a "one spot—one image" manner, wherein one image of on sample is required for the determination of the DNA-damage present in the sample. In particular only one single image of the spot is required for determining the DNA-damage. In other words: One shot respectively image, namely one photo, is take from one spot, namely one sample, including the single cells.

A one spot—one image determination according to the prior art is not possible. This is because the depth of field of the image is not sufficient. According to the prior art several images with varying depth of field have to be taken in order to determine the DNA-damage, as described, e.g., by Gyori et. al, Redox Biology 2 (2014) 457-465.

According to the one shot-one image evaluation an automated analysis can be performed. This strengthens the meaningfulness of the single cell gel electrophoresis ("comet assay") test. According to the prior art several pictures have to be taken from different positions and/or different depth of field.

A stitching of pictures form different positions of the single spot can lead to artefacts in the overall image, influencing the evaluation of the DNA-damage and reducing the reproducibility of the results. Accordingly, the edge respectively overlapping region of the stitched image should not be evaluated, leading to reduced set of possible cells ("comet") available for evaluation. Furthermore also distortion effects can be introduced by the stitching and the evaluation of separated imaged. Even without stitching and individual evaluation of the separate images/pictures of one spot care has to be taken with respect to the double evaluation of cells ("comets") in the region of potential overlap of the individual images.

Additionally, an overlap of spots can occur due to a different location in the depth of the spot. Such an overlap of the cells ("comets") makes it impossible to evaluate any of the overlapping cells, as for example shown in Gyori et. al, Redox Biology 2 (2014) 457-465; FIG. 1B.

All these factors reduce the reproducibility of an evaluation with several (5-20) images per spot.

The one shot-one image approach benefits from a high sensitivity and/or reproducibility of the single cell gel electrophoresis. Therefore, the comet assay can be performed at a low concentration of single cells. This results in a dilution separation of the cells diminishing the overlap of cell in different depth of the spot/sample.

Furthermore, if the spot is not flattened and/or not levelled the size of the spot is relatively small. This can promote the one spot-one image approach, as it is easier to take a single shot from a smaller spot than from a larger spot.

The cell concentration in the sample can be 200-400 cells per sample. Due to the low concentration an inter-cell influence can be reduced. In contrast to that prior art recommends 8000-10000 cell per spot (Gyori et. al, Redox Biology 2 (2014), page 463—"recommendation for preparing slides").

Due to a high sensitivity it is also possible that only a small sample volume. The sample volume can be 15 μL or less per spot/aliquot, in particular at least one of 8 μL to 7 μL, and 5 μL or less per spot/aliquot. Accordingly a lower superposition of the cells can be caused by the same cell concentration due to the lower agarose/sample layer thickness. Therefore, in the Z-direction (axis descends for absorption) fewer cells per area can be detected compared to the prior art. In contrast to that the mere dilution of the sample, as described in SIGNE BRAAFLAOT ET AL; "The Comet Assay: Automated Imaging Methods for Improved Analysis and Reproducibility", SCIENTIFIC REPORTS, vol. 6, no. 1, 1 Sep. 2016 (2016-09-01). Additionally, in a rather big spot as 30 μL the evaluation of the DNA damage might be complicated, as stitching of the individual subpictures of the sample becomes difficult at low cell concentration. Furthermore, as state of the art live images are evaluated without taking any pictures for big spots. In such a case the data cannot be reproduced, as no imaging is available for subsequent evaluation. Accordingly, data obtained by live images are not traceable.

The DNA-damage can determined in correlation with an UV-intensity applied to the sample before performing the single cell gel electrophoresis. The UV light can introduce additional DNA-damages, inducing major genetic lesions in the cell.

The DNA-damage can be determined in a cell of the liquid sample of the subject.

The screening can be utilised in personalised medical therapy, where a single subject can be screened and/or a bio-monitoring, where a huge number of subjects representing a defined/specific population can be screened.

The personalised medical therapy can also be called personalized medicine, individualized therapy. The therapy itself can also be a medical treatment.

The bio-monitoring can also be called human biomonitoring and/or environmental biomonitoring.

The method for screening a subject for at least a (specific) DNA-damage in relation to a predisposition for and/or a presence of a disease includes the steps of:
providing carrier plate and a liquid sample;
wherein the liquid sample includes cells of the subject;
providing a gel electrophoresis device;
performing a single cell gel electrophoresis on the sample of the subject;
determining the DNA-damage with a high reproducibility with coefficient of variation CV of 15% or less.

As described above, the gel electrophoresis device is at least capable of:
positioning at least one carrier plate in a homogenous electrical field generated by at least one pair of electrodes; and
controlling strength and direction of the electrical field generated at the position of the samples accommodated on the carrier plate.

The single cell gel electrophoresis can be performed on the sample of the subject by:
positioning the sample accommodated on the carrier plate in the generated homogenous electrical field and
controlling strength and direction of the electrical field while the sample is positioned in the gel electrophoresis device.

The screening can be a high throughput screening, wherein a large number of samples can be evaluated.

The screening can be performed on at least two aliquots of the subject liquid sample. In other words: At least two aliquots of the sample can be screened for evaluation/determination of the DNA-damage, as described above.

BRIEF DESCRIPTION OF THE DRAWINGS

The subject matter of the invention will be explained in more detail in the following text with reference to exemplary embodiments which are illustrated in the attached drawings, in which.

DETAILED DESCRIPTION OF THE INVENTION

Figure 1:
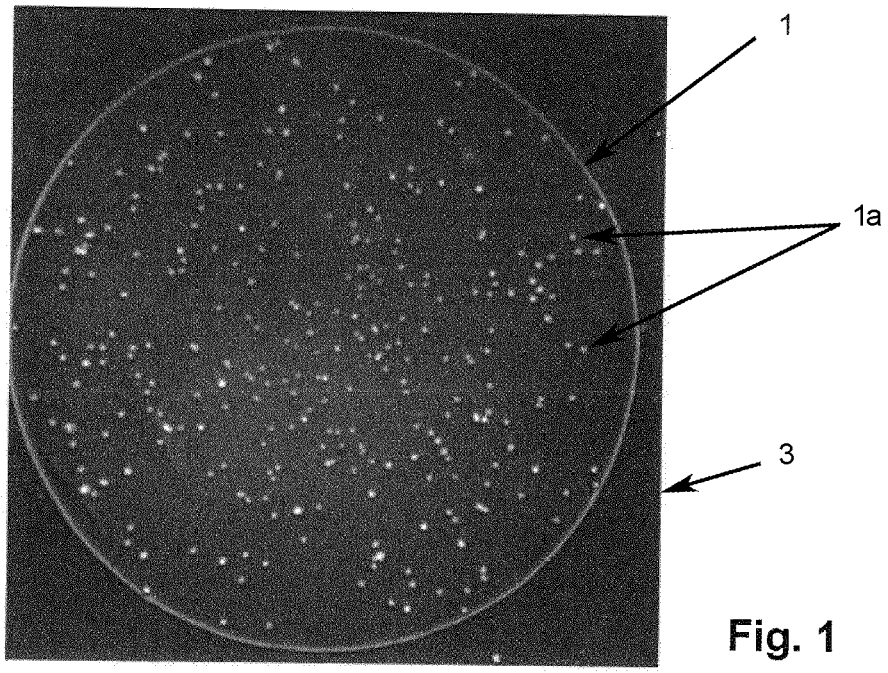
FIG. 1 single spot.

The reference symbols used in the drawings, and their meanings, are listed in summary form in the list of reference symbols. In principle, identical parts are provided with the same reference symbols in the figures.

FIG. 1 shows a whole single spot 1 of a liquid sample on a carrier plate 3. The liquid sample includes cells 1a of a subject to be screened. The screening is conducted to screen a subject for at least a (specific) DNA-damage in relation to a predisposition for and/or a presence of a disease.

The term single shot is represented as a single image respectively single photo taken from the sample.

The liquid sample is applied on the carrier plate. The carrier plate is positioned in a homogenous electrical field generated by at least one pair of electrodes of a gel electrophoresis device. By controlling strength and direction of the electrical field generated at the position of the samples accommodated on the carrier plate a single cell gel electrophoresis (SCGE) is performed. The single cells are depicted as whitish dots. The dots are also called comets, as the single cell gel electrophoresis (SCGE) is also called comet assay.

The positioning of the carrier plate, respectively the liquid sample, and the controlling of the electrical field is performed by a single cell gel electrophoresis device (not shown).

Figure 2:
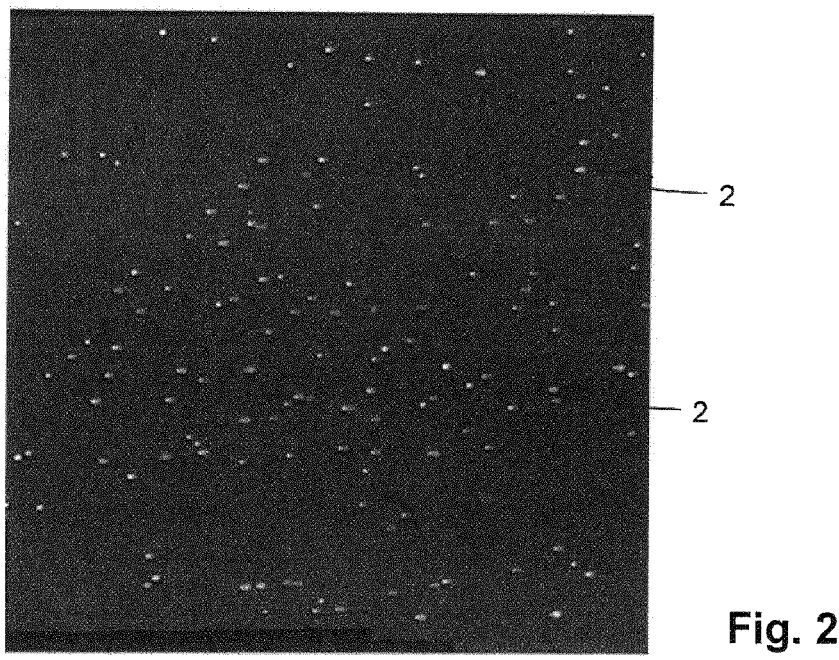
FIG. 2 section of the single spot of FIG. 1.

FIG. 2 shows a section of the single spot of FIG. 1. The single comets 2, each representing a single cell, show a head on the left side and a tail at the right side. The orientation of the comet depends on the orientation of the single cells in the electrical field. From the ratio between the tail and the head of the comet/single cell the DNA-damage can be determined.

The concentration in the spot is approximately 200-400 cell per sample. Accordingly, an overlap of individual comets is minimized compared to the prior art (Gyori et. al, Redox Biology 2 (2014)), where at least a ten-fold of cells is recommended. A corresponding output image according to the prior art (FIG. 1B/Gyori et. al, Redox Biology 2 (2014)) shown in FIG. 3.

Figure 3:
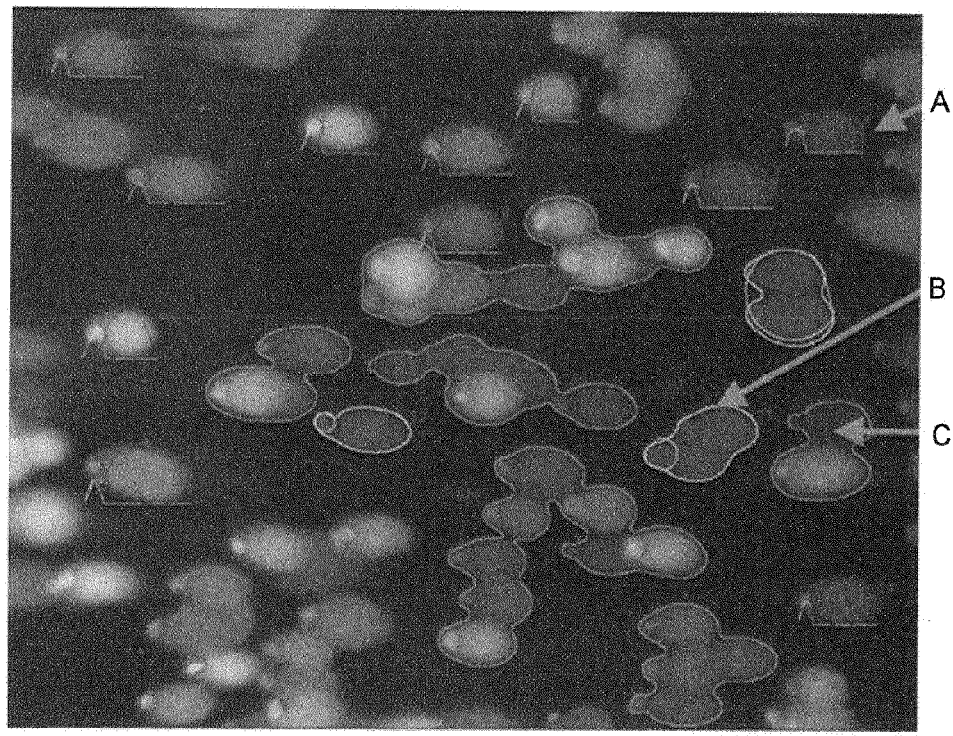
FIG. 3 prior art image of sectional spot.

FIG. 3 shows a section of a spot in an image with valid comets (A), invalid comets (B) and outlier comets (C). The overlap of several comets for example in different depth of the sample results in outlier comets and invalid comets. Such comet (B and C) cannot be evaluated and a determination of the DNA-damage is not possible for a significant number of cells/comets.

Figure 4:
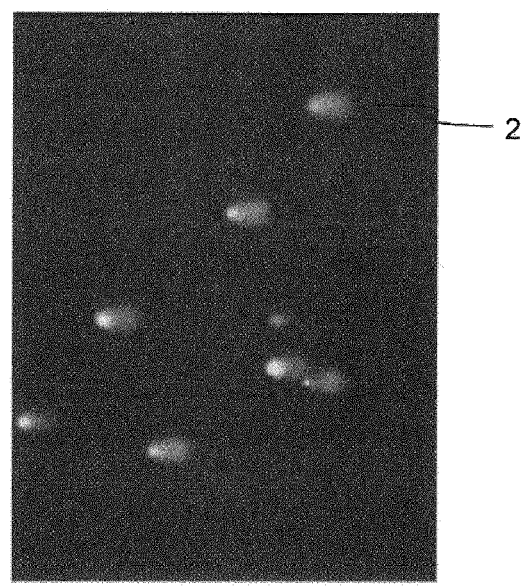
FIG. 4 close view of a single spot as depicted in FIG. 1.

In contrast to that according to the claimed invention the comets/cell are separated from each other and an overlap also in the depth of the sample can be minimized (see FIG. 4). This can lead to a more reliable and/or easy to automatize evaluation of the comets/single cells in the liquid sample. Accordingly, the DNA-damage of the screened liquid sample can by highly reproducible.

Prior art documents as Azqueta et al.: *A comparative performance test of standard, medium-and high-throughput comet assays*; Toxicology in Vitro, volume 27, pp. 768-773, 2013 (short: Azqueta et al.) and Collins et al.: Controlling variation in the comet assay; frontiers in Genetics, volume 5, article 359, October 2014 (short: Collins et al.) describe the current common knowledge of standardisation and potential for optimisation regarding the precision of the comet assay.

Collins et al. describes a method for standardising the treatment of the tested cells. Two partner laboratories (short: labs) carried out experiments with TK-6 lymphoblastoid cells treated with 0.25 mM methylmethanesulphonate (MMS) for 3 h. Furthermore the sample is biological influenced and therefore not applicable to an arbitrary experiment, but is manipulating the biological properties of the cells. This limits the application of Collins method for usage in real screening a subject for a DNA-damage in relation to a predisposition and/or presence of a disease. Such a manipulation is depends to a high degree on the activity and specificity of the enzyme used for the treatmant of the cells, as for example formamidopyrimidine DNA glycosylase (FPG) converts 8-oxoguanine and some other oxidised purines to breaks. Depending on the enzyme more or less breaks are produced which are building the comet in the evaluated comet assays.

As stated by Collins et al. page 3, right column: "one laboratory had more variable results than the other". According to data shown by Collins the determined DNA-damage between two labs differs roughly by a factor of 2 to 3 meaning by roughly 30%. Such a CV is also called lab-to-lab coefficient of variation. The lab-to-lab CV can be view as inter-laboratory comparison giving an inside on the actual reproducibility of the determined DNA-damage.

In contrast to that according to the claimed invention the a lab-to-lab coefficient of variation (CV) can be 15% or less, in particular 10% or less, in particular 8% or less, in particular 7.5% or less, in particular 5% or less, in particular 3% or less, in particular 2% or less, in particular 1% or less.

Figure 5:
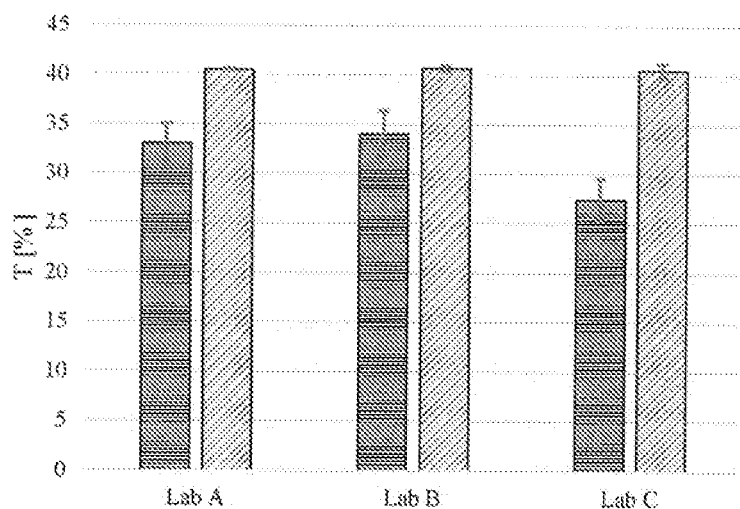
FIG. 5 bar diagram with DNA-damage in % for three labs.

FIG. 5 shows the determined DNA-damage in % as % DNA in tail (T) for three labs, namely LabA, LabB and LabC in a bar chart, wherein data according to prior art is depicted as horizontally striped and data according to the present invention is depicted as diagonally striped bars. It can be seen, that the variation in the data according to prior art (Azqueta et al.) varies significantly more, than the data obtained according to the invention. TK-6 cells (human-derived lymphoblastoid cell line) were used for the experiments. TK-6 is a popular cell line.

Due to the high reproducibility a biological variance in the screened liquid sample of the subject can be evaluated. In contrast to that, according to the prior art (horizontally striped bars in FIG. 5) the biological variance is covered by the variation of the single cell gel electrophoresis and the subsequent determination of the DNA-damage. The high reproducibility makes the use of the screening according to the invention reliable and applicable to other systems and evaluations. The low lab-to-lab coefficient of variation enables a determination of the DNA-damage and a corresponding screening of a subject for a DNA-damage in relation to a predisposition for and/or a presence of a disease.

Based on the high variation between the different labs, Collins' data require an internal standard, as already mentioned by Collins. This is not the case for the highly standardised and highly reproducible method and use according to the invention, which offers a timely stable and homogenous field. It can also include a well-defined and strict protocol including ready to use reagents. Any internal standard would only be used to make sure that the assay is working appropriate.

Figure 6:
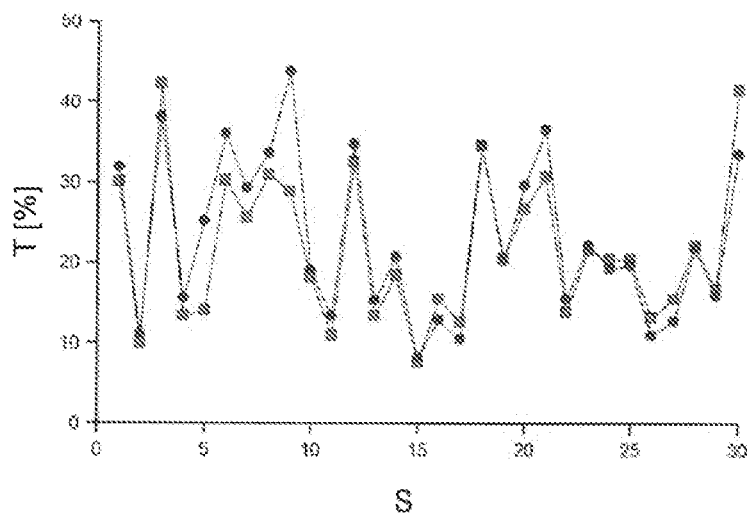
FIG. 6 prior art image of DNA-damage (T) of 30 samples (S)
Figure 7:
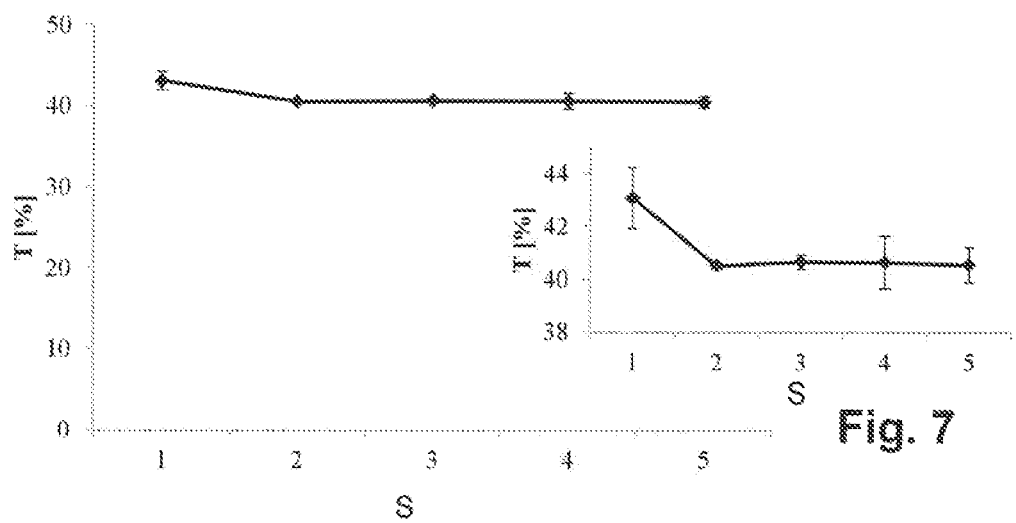
FIG. 7 diagram showing DNA-damage (T) several samples (S).

According to Collins et al. the data of the comet assay vary from spot-to-spot quiet significantly, as shown reproduced in FIG. 6 (corresponding to FIG. 3 of Collins et al.). In FIG. 6 the DNA-damage (T) of 30 samples (S) is depicted in %, wherein the squared represent data without and the circles data with a normalization according to the prior art. In contrast to that FIG. 7 shows a similar set of data for 5 samples (S). The insert depicts an enlarged section of data shown FIG. 7. The data according to the present invention (FIG. 7) show a significant smaller variation than data according to prior art (FIG. 6). Accordingly, the reproducibility on a spot-to-spot basis improved in the present invention. The spot-to-spot coefficient of variation (CV) can be 15% or less, in particular 10% or less, in particular 8% or less, in particular 7.5% or less, in particular 5% or less, in particular 3% or less, in particular 2% or less, in particular 1% or less. In this context spot-to-spot CV can be viewed as variation of the determined DNA-damage on a spot-to-spot basis. A spot being one liquid sample respectively one aliquot of the liquid sample screened.

Additionally, also an evaluation of the DNA-damage on a plate-to-plate basis gives rise to a coefficient of variation (CV) which can be 15% or less, in particular 10% or less, in particular 8% or less, in particular 7.5% or less, in particular 5% or less, in particular 3% or less, in particular 2% or less, in particular 1% or less. The plate-to-plate CV can be determined form single spots (aliquots) arranged on different carrier plates. The results are similar to the once shown in FIG. 7.

State of the art determination of a DNA-damage can be performed on none manipulated cell sample with an average damage with a coefficient of variation of approximately 30-40%. According to the claimed invention the coefficient of variation (CV) of 15% or less can also be obtained. Such a CV can also be obtained in disproportionally (over- or under-proportionally) damaged cells, as for example a simulated damage introduced by X-ray.

While the invention has been described in present preferred embodiments of the invention, it is distinctly understood that the invention is not limited thereto, but may be otherwise variously embodied and practised within the scope of the claims.

The invention claimed is:

1. A method for screening cells of a subject for DNA-damage comprising the steps of:
    depositing a liquid sample comprising cells of the subject in at least one spot on a carrier plate, wherein the at least one spot contains a volume of 15 µL or less of the liquid sample, and wherein the at least one spot includes 75 to 400 cells of the subject to be evaluated for DNA-damage;
    performing single cell gel electrophoresis on the at least one spot deposited on the carrier plate; and
    determining DNA-damage for the cells of the subject present in the at least one spot based on an analysis of comets appearing in a single image taken of the at least one spot after single cell gel electrophoresis.

2. The method according to claim 1, wherein the liquid sample deposited on the carrier plate is not flattened on the carrier plate by a cover plate and/or a cover slide.

3. The method according to claim 1, wherein the liquid sample comprising cells of the subject is deposited in two or more spots on the same carrier plate, wherein the two or more spots each contains a volume of 15 µL or less of the liquid sample, wherein the two or more spots each include 75 to 400 cells of the subject to be evaluated for DNA-damage, wherein single cell gel electrophoresis is performed on the two or more spots deposited on the carrier plate, and wherein DNA-damage for the cells of the subject present in the two or more spots is determined based on an analysis of comets appearing in single images taken of the two or more spots after single cell gel electrophoresis.

4. The method according to claim 3, wherein a spot-to-spot coefficient of variation for the determination of DNA-damage is 15% or less.

5. The method according to claim 1, wherein before the liquid sample comprising cells of the subject is deposited in at least one spot on the carrier plate, a cell separation step is performed on the liquid sample such that only lymphocytes and/or biomarker carrier cells remain in the liquid sample for deposition on the carrier plate.

6. The method according to claim 1, wherein the analysis of comets appearing in the single image taken of the at least one spot after single cell gel electrophoresis to determine DNA-damage for the cells of the subject present in the at least one spot based is automated.

7. The method according to claim 1, wherein the at least one spot includes 100 to 400 cells of the subject to be evaluated for DNA-damage.

8. The method according to claim 1, wherein the at least one spot includes 200 to 400 cells of the subject to be evaluated for DNA-damage.

9. The method according to claim 1, wherein the at least one spot includes 75 to 200 cells of the subject to be evaluated for DNA-damage.

10. The method according to claim 1, wherein the at least one spot includes 100 to 200 cells of the subject to be evaluated for DNA-damage.

11. The method according to claim 1, wherein the at least one spot includes 75 to 100 cells of the subject to be evaluated for DNA-damage.

12. The method according to claim 1, wherein the screening method is utilized in a personalized medical therapy for the subject and/or in bio-monitoring of the subject.

13. A method for screening cells of a subject for DNA-damage comprising the steps of:
    performing single cell gel electrophoresis on at least one spot of a liquid sample comprising cells of the subject deposited on a first carrier plate and on at least one spot of the liquid sample comprising cells of the subject deposited on a second carrier plate, wherein each of the spots contains a volume of 15 µL or less of the liquid sample, wherein each of the spots includes 75 to 400 cells of the subject to be evaluated for DNA-damage; and
    determining DNA-damage for the cells of the subject present in the spots based on an analysis of comets appearing in single images taken of the spots after single cell gel electrophoresis;
    wherein a coefficient of variation for the determination of DNA-damage, carrier plate-to-carrier plate, is 15% or less.

14. The method according to claim 13, wherein single cell gel electrophoresis is performed on the at least one spot deposited on the first carrier plate by a first lab, wherein single cell gel electrophoresis is performed on the at least one spot deposited on the second carrier plate by a second lab that is different than the first lab, and wherein a coefficient of variation for the determination of DNA-damage, lab-to-lab, is 15% or less.

15. A method for determining biological variance between a first subject and a second subject, the method comprising:
    performing single cell gel electrophoresis on at least one first spot a liquid sample comprising cells of the first subject deposited on a carrier plate and on at least one second spot of a liquid sample comprising cells of the second subject deposited on a carrier plate that is the same as or different than the carrier plate on which the liquid sample comprising cells of the first subject is deposited, wherein the first spot contains a volume of 15 µL or less of the liquid sample comprising cells of the first subject, wherein the second spot contains a volume of 15 µL or less of the liquid sample comprising cells of the second subject, wherein the first spot includes 75 to 400 cells of the first subject, and wherein the second spot includes 75 to 400 cells of the second subject;

determining DNA-damage for the cells of the first subject present in the at least one first spot based on an analysis of comets appearing in a single image taken of the at least one first spot after single cell gel electrophoresis, and determining DNA-damage for the cells of the second subject present in the at least one second spot based on an analysis of comets appearing in a single image taken of the at least one second spot after single cell gel electrophoresis; and determining the biological variance between the first subject and the second subject based on the determined DNA-damage for the cells of the first subject and the second subject.

16. The method according to claim 15, wherein the biological variance determined between the first subject and the second subjection indicates a predisposition for and/or the presence of a disease in one of the first subject and the second subject.

* * * * *